United States Patent [19]

Allphin et al.

[11] 4,239,930

[45] Dec. 16, 1980

[54] CONTINUOUS OLIGOMERIZATION PROCESS

[75] Inventors: N. Lee Allphin, Pinehurst; Fred S. Valentine, Houston; Gary W. Grams, Spring, all of Tex.

[73] Assignee: Pearsall Chemical Company, Houston, Tex.

[21] Appl. No.: 39,832

[22] Filed: May 17, 1979

[51] Int. Cl.$^3$ .............................................. C07C 2/02
[52] U.S. Cl. ..................................... 585/517; 585/525
[58] Field of Search ............................... 585/517, 525

[56] References Cited

U.S. PATENT DOCUMENTS

| | | | |
|---|---|---|---|
| 3,780,128 | 12/1973 | Shabkin | 585/355 |
| 3,876,720 | 4/1975 | Heilman et al. | 585/520 |
| 3,997,621 | 12/1976 | Brennan | 585/510 |
| 4,045,507 | 8/1977 | Cupples et al. | 585/511 |
| 4,045,508 | 8/1977 | Cupples et al. | 585/511 |

*Primary Examiner*—Curtis R. Davis
*Attorney, Agent, or Firm*—Arnold, White & Durkee

[57] ABSTRACT

Alpha-olefins are oligomerized to a product useful as a synthetic lubricant in a continuous process utilizing a promoted boron trifluoride catalyst. The oligomerization is carried out in a system comprising a plurality of loop recycle reactors arranged in series, the reaction being preferably carried out such that:

(A) The total residence time of alpha-olefin monomer/oligomerization product in the system is from about 1 to about 2 hours; and (B) The flow rate through each of the plurality of loop recycle reactors effects a turnover of reactor contents of each reactor at least once every 5 minutes.

15 Claims, 1 Drawing Figure

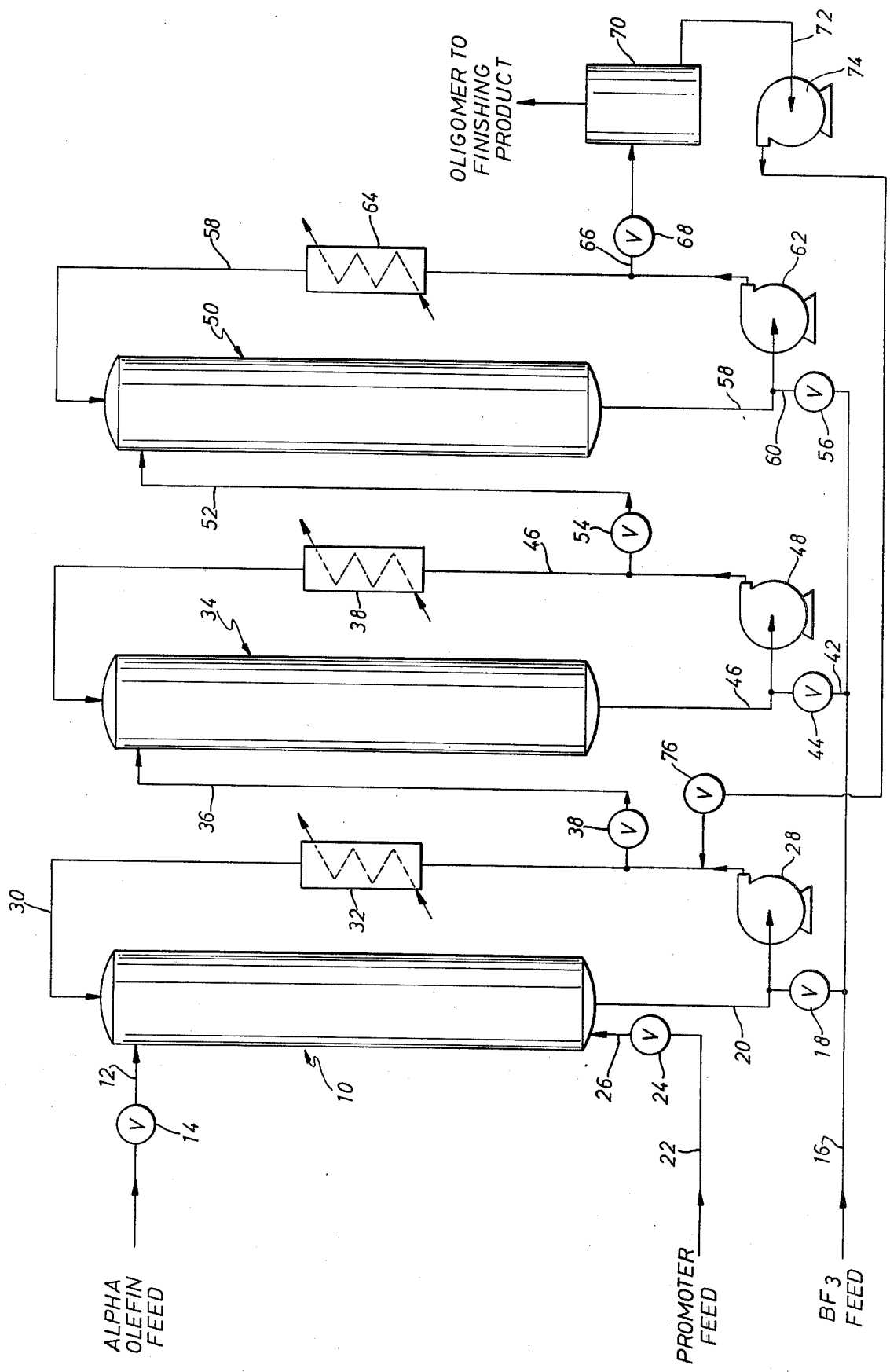

CONTINUOUS OLIGOMERIZATION PROCESS

CROSS-REFERENCE TO RELATED APPLICATION

During experimentation in connection with this invention, and in particular in connection with the development of specific parameters and a system to allow recycle of promoted boron trifluoride catalyst, Gary W. Grams and Fred S. Valentine, employed by Pearsall Chemical Corporation, assignee of this application, separately developed a system for centrifugal separation of the promoted boron trifluoride catalyst from the oligomer product. That invention developed by Grams and Valentine will be described hereinafter in connection with the best mode for separation of promoted boron trifluoride catalyst from the oligomerization product and return of the promoted catalyst to the reactor system. That invention developed Grams and Valentine is the subject of their application, also assigned to Pearsall Chemical Corporation filed concurrently herewith under Ser. No. 039,829 and entitled "Continuous Oligomerization With Catalyst Separation And Recycle".

BACKGROUND OF THE INVENTION

1. Field of the Invention

This invention relates to the oligomerization of alpha-olefins, such as 1-decene, and more particularly, this invention relates to the use of a loop recycle reactor system for the continuous oligomerization process.

2. Description of the Prior Art

Olefin oligomers have been previously proposed and used as synthetic lubricants. The oligomers of alpha-olefin containing from 8 to 12 carbon atoms are generally used in the preparation of these lubricants with, more specifically, the trimer of 1-decene being most useful in preparing lubricants for use in hydraulics, transmissions, transformers and the like.

Various processes have been developed in the past for the oligomerization of such alpha-olefins to produce synthetic lubricants and like products. Among these processes are those which employ a promoted boron trifluoride catalyst for the oligomerization reaction. Until recently, all of the processes developed for the oligomerization of alpha-olefins were batch processes, utilizing a variety of chemicals to promote the boron trifluoride catalyst. Representative processes for example are described in the following United States patents:

U.S. Pat. No. 2,183,503—McAlevy
U.S. Pat. No. 2,766,312—Serniuk
U.S. Pat. No. 2,552,508—Peters
U.S. Pat. No. 2,816,944—Muessig et al.
U.S. Pat. No. 3,149,178—Hamilton et al.
U.S. Pat. No. 3,382,291—Brennan
U.S. Pat. No. 3,742,082—Brennan
U.S. Pat. No. 3,763,244—Shubkin While each of the processes set forth in the above patents is somewhat effective in producing the desired synthetic lubricant, with varying degrees of success, each of the processes has the disadvantage that it is batch process. More recently, continuous processes for the oligomerization of alpha-oleins have been proposed. For example, U.S. Pat. No. 4,045,507 to Barrett L. Cupples, et al, and U.S. Pat. No. 4,045,508, also to Barrett L. Cupples, et al, both of which are assigned to Gulf Research and Development Company, disclose continuous processes for the oligomerization of alpha-olefins to produce a synthetic lubricant product. The Cupples U.S. Pat. No. 4,045,507 utilizes a series of at least two flow-through tank reactors for the continuous multi-stage alpha-olefin oligomerization. In accordance with this process, the 1-olefin and catalyst are introduced into and mixed together in a tank reactor for partial oligomerization and the reaction product from this first tank reactor is directed to one or more additional tank reactors in series for completion of the oligomerization.

The Cupples U.S. Pat. No. 4,045,508 also discloses a continuous oligomerization process. The process of this U.S. Pat. No. 4,045,508, however, differs from that disclosed in the U.S. Pat. No. 4,045,507 in that the partial oligomerization product from the first tank reactor is thereafter passed through a final tube reactor in order to complete the oligomerization. The processes of both patents are said to allow continuous oligomerization and control over the trimer to tetramer ratio of the final synthetic lubricant product.

A continuous process for the oligomerization of alpha-olefins to produce a synthetic lubricant product is also disclosed in a draft report of A. Sacks of SRI entitled "Synthetic Lubricants". This draft report, a copy of which can be supplied by applicant, surveys the various processes which have been previously proposed for both batch and continuous oligomerization of alpha-olefins to produce a synthetic lubricant product. The draft report proposes a model process for the continuous oligomerization of alpha-olefins, utilizing as a basis for this model the series of tank reactors as described in the Cupples U.S. Pat. No. 4,045,507 assigned to Gulf Research and Development Company. The various prior art descriptions and other features of this draft report are incorporated herein by reference.

The use of loop recycle reactors in series for chemical conversion is also known. For example, Pearsall Chemical Corporation, the assignee herein, has issued to it U.S. Pat. No. 4,052,471 in the name of Mason P. Pearsall which describes the use of a loop recycle reactor system for chlorinating substantially linear liquid $C_8$ to $C_{30}$ hydrocarbons. The system illustrated in the Pearsall Chemical Corporation patent has been commercially utilized for the chlorination of substantially linear liquid hydrocarbons in the LaPorte, Texas plant of Pearsall Chemical Corporation. Applicant, however, is unaware of any prior suggestion of the use of a loop recycle reactor system for the oligomerization of alpha-olefins or the advantages which applicant has found to be achieved through that system.

SUMMARY OF THE INVENTION

It has now been discovered in accordance with the present invention that an improved process for the continuous production of synthetic lubricants by the oligomerization of alpha-olefins can be provided, utilizing a promoted boron trifluoride catalyst, by carrying out the oligomerization in a system which comprises a plurality of loop recycle reactors in series. This process is preferably carried out in accordance with the present invention, such that (a) the total residence time of alpha-olefin monomer/oligomerization product in the loop recycle reaction system is from about 1 to 2 hours; and (b) the flow rate through each of the plurality of loop recycle reactors effects a turnover of contents in each reactor at least once every five minutes, preferably at least once every three minutes.

It has been discovered in accordance with the present invention that the use of the loop recycle reactors in series provides for more efficient mixing of catalyst and alpha-olefin than possible with conventional batch systems or the tank reactors or tank and tube reactors as suggested by Gulf Research and Development Company. This increased mixing allows for better utilization of promoted boron trifluoride catalyst in the oligomerization process and allows for more effective control over the oligomerization process. Moreover, this more effective mixing which is achieved utilizing the plurality of loop recycle reactors in series allows the effective utilization of promoted boron trifluoride catalysts which are less soluble in the alpha-olefin monomer and oligomerization product. Also, economic advantages can be achieved in accordance with the present invention, along with the increased efficiency which is associated with the continuous nature of the present process and the enhanced catalyst utilization achieved with the loop recycle reactor system.

Moreover, the use of the loop recycle reactor system, with its ability to utilize less-soluble promoted boron trifluoride catalysts, provides for a more efficient separation of catalyst from oligomerization product than heretofore possible with conventional processes. Whereas, caustic washing and/or distillation were previously employed for removal of catalysts from the oligomerization product, in accordance with the present invention, physical separation of catalyst, with recycle of catalyst to the loop recycle reactor system can be effectively achieved. The use of this physical separation, specifically centrifugation, is described in greater detail in the co-pending application of Fred S. Valentine and Gary W. Grams, co-assigned herewith, which application is specific to the improvement associated with centrifugal separation of the catalyst from the oligomerization product and the recycle of that catalyst for further use in the oligomerization process.

BRIEF DESCRIPTION OF THE DRAWING

The single FIGURE illustrations in flow diagram form the present loop recycle reactor system and its utilization in the oligomerization of alpha-olefins.

DESCRIPTION OF THE PREFERRED EMBODIMENT

In the broadest sense, the present invention provides an improved process for the continuous oligomerization of alpha-olefins, so as to obtain a synthetic lubricant or similar product having a desirable oligomer distribution, utilizing a promoted boron trifluoride catalyst. The improvement in accordance with the present invention resides in carrying out the oligomerization in a system which comprises a plurality of loop recycle reactors in series. As described previously, such loop recycle reactor system provides enhanced mixing of the promoted boron trifluoride catalyst and alpha-olefin-/oligomerization product, thereby effecting increased and more effective catalyst utilization and enhanced efficiency in the oligomerization.

Prior to discussing the oligomerization process of the present invention by reference to the FIGURE, various parameters and materials will be discussed below:

ALPHA-OLEFIN FEEDSTOCK

The alpha-olefin feedstock which is utilized in the continuous oligomerization process of the present invention can be any alpha-olefin which has been typically utilized to produce an oligomerized product for synthetic lubricant purposes. Broadly described, the alpha-olefins useful in the present invention are those which have from about 5 to about 14 carbon atoms, as well as mixtures of these alpha-olefins.

In the production of synthetic lubricants from the preferred alpha-olefin, 1-decene, the trimer, tetramer and often times pentamer are of particular importance; as a result, the 1-decene oligomers particularly useful in the process of the present invention are those which provide effective synthetic lubricant products with a predominence of trimer and tetramer. Accordingly, for preparation of a synthetic lubricant product, it is preferred that the feedstock alpha-olefin in accordance with the present invention have from about 8 to about 12 carbon atoms with mixtures thereof. The most preferred alpha-olefin for use in the oligomerization process for the present invention is 1-decene, either alone or as the predominant component in a mixture of alpha-olefins of from about 8 to about 12 carbon atoms. It should be recognized, however, that the advantages with respect to the continuous production of an oligomerization product in accordance with the present invention utilizing the plurality of loop recycle reactors can be achieved when employing as the feedstock any of the alpha-olefins typically utilized in oligomerization processes.

THE PROMOTED BORON TRIFLUORIDE CATALYST

Gaseous boron trifluoride is utilized as the catalyst in the continuous oligomerization process of this invention. The boron trifluoride is utilized with a compound which is typically referred to as a promoter or co-catalyst. This co-catalyst or promoter is conventional in oligomerization processes and typically can be any compound which complexes with boron trifluoride to form a coordination compound which is catalytically active in the oligomerization reaction.

Included in this list of co-catalysts are aliphatic ethers, such as dimethyl ether, diethyl ether and the like; aliphatic alcohols such as methanol, ethanol, n-butanol, decanol, and the like; polyols, such as ethylene glycol, glycerol and the like; water; aliphatic carboxylic acids such as acetic acid, propanoic acid, butyric acid, and the like; esters, such ethyl acetate, methyl propionate, and the like; ketones, such as acetone and the like; aldehydes, such as acetaldehyde, benzaldehyde, and the like; acid anhydrides, such as acetic acid anhydride, succinic anhydride, and the like; etc.

In accordance with the present invention, it is preferred to utilize as the co-catalyst or promoter for the boron trifluoride one of the lower aliphatic carboxylic acids, low molecular weight alcohols, or water. Particularly preferred in accordance with the present invention are the alcohol co-catalysts, with the most-preferred embodiment of the present invention involving the utilization of ethanol as the co-catalyst or promoter for the boron trifluoride catalyst.

It is a unique feature of the present invention that the ethanol promoter or co-catalyst can be effectively utilized in the continuous oligomerization process. Ethanol has been proposed in various prior art references as the co-catalyst for boron trifluoride in oligomerization of alpha-olefins; its use, however, has been very limited in view of the rather low solubility of the boron trifluoride-ethanol complex in the alpha-olefin feedstock and oligomerization product. Certainly in batch processes, this limited solubility prevents effective utilization of the boron trifluoride-ethanol complex. Even in previously proposed continuous processes for alpha-olefin oligomerization, mixing of the complex with the alpha-olefin feedstock and oligomerization product using conventional stirred tank reactors has been insufficient for effective utilization of the boron trifluoride-ethanol complex.

In accordance with the present invention, however, the use of the plurality of loop recycle reactors in series in the continuous oligomerization of the alpha-olefin provides very effective mixing of the boron trifluoride-ethanol complex with the alpha-olefin feedstock and oligomerization product. Accordingly, this system allows effective utilization of this complex catalyst, which is extremely effective for oligomerization and production of the desired synthetic lubricant product. In addition, as will be explained hereinafter by reference to the FIGURE, the use of the less soluble boron trifluoride-ethanol complex provides for advantageous separation of the catalyst complex from the oligomerization product, thereby providing for recycle of the catalyst complex and more enhanced catalyst utilization.

The boron trifluoride need be utilized as a catalyst only in that amount effective to achieve the desired oligomerization. In general, the boron trifluoride gas is employed in an amount to provide adequate pressure to saturate the alpha-olefin feedstock and promoter or co-catalyst utilized with the boron trifluoride. The pressure of the boron trifluoride, however, should not be so high that special high-pressure reactors and lines are needed to carry out the oligomerization reaction. The boron trifluoride is generally employed so as to provide a pressure in the reactor system of from about 2 to about 100 psi, with pressures of about 10 psi being found to be particularly advantageous.

The co-catalyst or promoter that is utilized together with the boron trifluoride in the instant oligomerization reaction is utilized in an amount effective to promote the oligomerization. It has been found in accordance with the present invention that the amount of this co-catalyst or promoter should be from about 0.01 weight percent to about 3.0 weight percent based upon the weight of the alpha-olefin feedstock. A particularly effective amount of co-catalyst or promoter in accordance with the present invention has been found to be about 0.75 weight percent, based again on the weight of the alpha-olefin feedstock.

DESCRIPTION OF THE PREFERRED EMBODIMENTS BY REFERENCE TO ATTACHED FIGURE

The preferred embodiments of the present invention will now be described by reference to the attached FIGURE, which illustrates in flow diagram form the instant utilization of a plurality of loop recycle reactors to effect alpha-olefin oligomerization.

As illustrated in the FIGURE, the alpha-olefin feed (from a source not shown) is metered into a first loop recycle reactor 10 through line 12, the metering being controlled by valve 14. The FIGURE does not illustrate the mechanism for control of valve 14 and the other valves to be described hereinafter. In effect, any mechanical or electrical system for control of these valves can be utilized in carrying out the oligomerization reaction in accordance with the present invention. As will be described more specifically hereinafter, the flow of alpha-olefin feed through line 12 into first loop recycle reactor 10 is such that the flow rate substantially matches the withdrawal of oligomer product from the loop recycle reactor system. In this manner, the oligomerization process can be carried out on a continuous basis. Typical systems for effecting this flow in chemical processing are well known in the art.

The alpha-olefin feed introduced into the first loop recycle reactor 10 is preferably commercially available 1-decene, or a mixture of alpha-olefins of 8-12 carbon atoms containing a predominant amount of 1-decene. Such commercially available feedstocks generally contain a very minor amount of paraffin, n-decane, which does not interfere with the oligomerization reaction.

The boron trifluoride catalyst (from a supply not illustrated) is introduced into recycle line 20 of the first loop recycle reactor 10 from BF$_3$ feed line 16 by means of valve 18. Again, valve 18 is regulated in a conventional manner such that the boron trifluoride feed effects a saturation of the alpha-olefin feedstock and promoter or co-catalyst employed in conjunction with the boron-trifluoride. In a preferred embodiment of the present invention, the feed of boron trifluoride is such as to provide a pressure in each of the loop recycle reactors of about 10 psi.

The promoter or co-catalyst used in conjunction with the boron trifluoride (from a source not shown) is introduced into the first loop recycle reactor 10 from promoter feed line 22 by means of valve 24 and line 26. Valve 24 regulates the flow of the promoter or co-catalyst in a conventional manner such that the amount of the promoter or co-catalyst is within the range of 0.01 weight percent to 3.0 weight percent based on the weight of the alpha-olefin feedstock. About 0.75 weight percent of the promoter or co-catalyt has been found particularly effective, especially when utilizing the preferred co-catalyst, ethanol.

As will be explained in more detail hereinafter, the preferred promoter or co-catalyst in accordance with the present invention is ethanol (specifically absolute ethanol containing no water) which is commercially available in a denatured form, containing up to about 5% isopropyl alcohol. This ethanol promoter or co-catalyst is particularly effective in accordance with the present invention in achieving the desirable high trimer content of the oligomer product, with a high ratio of trimer to tetramer, specifically a ratio of at least 2.5:1, oftentimes as high as 3:1. In addition, the use of the ethanol promoter or co-catalyst produces further advantages relating to separation of the boron-trifluoride-ethanol complex from the oligomerization product. This will be explained in more detail hereinafter.

Loop recycle reactor 10 as well as the other loop recycle reactors employed in the process of the present invention can be of any conventional design. Generally, however, the loop recycle reactors are those which have a height-to-diameter ratio of at least about 2:1, preferably from about 2:1 to about 12:1, although there is essentially no upper limit with respect to this height-to-diameter ratio. It is essential, however, that each loop recycle reactor allow intimate mixing of the alpha-olefin feedstock and boron trifluoride-promoter complex. This of course is necessary to achieve the desired oligomerization.

It is a characteristic feature of the present invention that the efficient mixing of the alpha-olefin feedstock and boron trifluoride-promoter complex is achieved by continuous recycle of reactor contents through a recycle loop associated with each of the reactors; hence the expression as used throughout "loop recycle reactor".

The recycle loop associated with loop recycle reactor 10 is illustrated in the FIGURE as follows. The contents of loop recycle reactor 10 i.e. the mixture of alpha-olefin feedstock, boron trifluoride-promoter complex and partial oligomerization product is withdrawn through line 20 and pumped by means of pump 28 back into loop recycle reactor 10 by means of line 30. In line 30, the recycling contents of loop recycle reactor 10 are passed through a suitable heat exchanger or cooling unit 32 wherein the recycling contents are subjected to cooling to remove the exothermic heat of the oligomerization reaction. Heat exchanger or cooler 32 can be of any conventional design, typically using cold water or brine as the cooling medium. The temperature of the recycling contents are cooled to a range of from about 10° to about 50° C. so as to maintain the contents within loop recycle reactor 10 within this range. Preferably, the temperature within this reactor is maintained within the range of 20°–30° C., although the particular temperature which is preferred depends to some extent on the promoter or co-catalyst which is utilized with the boron trifluoride catalyst. With respect to the use of the preferred ethanol promoter or co-catalyst, it has been determined that the temperature within each of the loop recycle reactors should be maintained within the range of 20°–30° C., preferably about 25° C. This produces the optimum yield of trimer and the highest possible trimer to tetramer ratio in the final oligomerization product.

As indicated previously, the use of the recycle loop associated with each of the loop recycle reactors effects efficient mixing between the alpha-olefin feedstock and oligomerization product thereof and the boron trifluoride-promoter complex. This recycle is constructed so that the contents of loop recycle reactor 10 are "turned over" at least once every 5 minutes, preferably at least once every 3 minutes. This is achieved, of course, by simply regulating the rate of pump 28 in relation to the volume of loop recycle reactor 10. In actuality, there is no limitation on how fast the contents of loop recycle reactor can be turned over and, better results are achieved with more efficient mixing, associated with a quicker turnover of the loop recycle reactor contents. It is likely that when this oligomerization process is carried out on a commercial scale, turnover of reactor contents in the order of 3–5 times each minutes will not be unusual.

Again, it should be recognized that the limitation on reactor turnover of at least once every 5 minutes is a practical limitation to achieve sufficient mixing between the alpha-olefin feedstock and boron trifluoride-promoter complex catalyst.

As illustrated in the FIGURE, a portion of the recycling contents in line 30 are passed into the second loop recycle reactor 34 through line 36. The flow into loop recycle reactor 34 through line 36 is controlled by means of valve 38. In effect, in carrying out the oligomerization process on a continuous scale, there will be a continuous flow of a portion of the recycling reactor contents from loop recycle reactor 10 through valve 38 and line 36 into the second loop recycle reactor 34. This flow will be controlled by a suitable level controller (not shown) in loop recycle reactor 10. This level controller can be of any conventional design to sense the level of contents in loop recycle reactor 10 to open valve 38 to provide a flow of recycling reactor contents through valve 38 and line 36 into loop recycle reactor 34.

Loop recycle reactor 34 can be of the same or different design as loop recycle reactor 10. Again, it is merely essential in accordance with the present invention that loop recycle reactor 34 provide an environment for effective mixing of its contents, including unreacted alpha-olefin feedstock, partial and complete oligomerization product and boron trifluoride-promoter complex. Preferably, each of the loop recycle reactors which are employed in the oligomerization system of the present invention is of the same or similar design.

Similarly, it is preferred in accordance with the present invention that the conditions which exist within loop recycle reactor 34 are the same, or essentially the same, as those which exist in loop recycle reactor 10. To achieve this, additional boron trifluoride is introduced into loop recycle reactor 34 from boron trifluoride feed line 16 by means of line 42, the flow of boron trifluoride being controlled by valve 44. As illustrated, the boron trifluoride is introduced into recycle loop line 46 through which the contents of loop recycle reactor 34 are continuously recycled by means of pump 48.

Again, the conditions within loop recycle reactor 34 are such as to provide a pressurized system wherein the boron trifluoride saturates the reactor contents, to a pressure of from about 2 psi to about 100 psi and the boron trifluoride promoter is present in an amount of about 0.01 weight percent to about 3.0 weight percent based on the alpha-olefin. The temperature within loop recycle reactor 34 is also controlled to be within the range of about 10° to 50° 1 C., preferably 20°–30° C., by passing the recycling contents of loop recycle reactor 34 in recycle loop 46 through a suitable heat exchanger or cooler 38, of the same or similar design as heat exchanger or cooler 32 employed in connection with loop recycle reactor 10.

It should be noted with respect to loop recycle reactor 34 that here again effective mixing of the catalyst with other reactor contents is achieved by providing a continuous recycle and turnover of the contents of loop recycle reactor 34 by means of pump 48 and recycle line 46. To achieve this effective mixing, the contents of loop recycle reactor 34 should be turned over at least once every 5 minutes, preferably at least once every 3 minutes.

As illustrated in the figure, a portion of the contents of loop recycle reactor 34 recycling through line 46 are withdrawn from recycle line 46 and introduced into the third loop recycle reactor 50 through line 52. The withdrawal of the recycling contents in line 46 and introduction into third loop recycle reactor 50 through line 52 is controlled by means of valve 54. As indicated with respect to the previously described loop recycle reactors, the operation of valve 54 is controlled by means of a suitable conventional level control device (not shown) within loop recycle reactor 34. In continuous operation of the oligomerization process of the present invention there will be a continuous flow of material into loop recycle reactor 50 from loop recycle reactor 34.

Loop recycle reactor 50 can be of the same or different design as the previously described loop recycle reactors 10 and 34. Preferably, however, loop recycle reactor 50 is of a same or similar design.

The only requirement is again that loop recycle reactor 50 be so constructed as to provide through the recycle loop effective mixing of the reactor contents, which in this case will include a lesser amount of alpha-olefin monomer, greater amounts of partial and complete oligomerization product and the boron trifluoride catalyst and promoter or co-catalyst.

While the figure illustrates the use of the three loop recycle reactors, it should be apparent that the oligomerization process of the present invention can be carried out with two or more such reactors, economics being the practical limit on the number of loop recycle reactors which are employed in series to achieve the desired alpha-olefin oligomerization. To achieve a final oligomer product having a high trimer content and a high ratio of trimer to tetramer from 1-decene, under the conditions which have been specified above, it appears that the use of three loop recycle reactors in series provides optimum results.

Conditions for oligomerization are achieved in loop recycle reactor 50 by introducing into loop recycle reactor 50 additional boron trifluoride from boron trifluoride feed line 16. The boron trifluoride is introduced into recycle line 58 through line 60, the flow of boron trifluoride being controlled by valve 56. Here again, the boron trifluoride should be present as to saturate the liquid contents of loop recycle reactor 50 with pressures of from 10 to 100 psi being applicable, with effective oligomerization being achieved with a pressure of 10 psi.

The contents within loop recycle reactor 50 will include some unreacted alpha-olefin feestock, partial and complete oligomerization product as well as the catalyst, the boron trifluoride-promoter complex. Further oligomerization of the alpha-olefins feedstock and partial oligomerization product is carried out in loop recycle reactor 50. Efficient mixing of the catalyst and other reactor contents is achieved by continuously turning over the contents of loop recycle reactor 50 through the recycle loop comprising line 58 and pump 62. The contents of loop recycle reactor 50 are continuously withdrawn through line 58 and returned by means of pump 62 to loop recycle reactor 50. In a manner similar to loop recycle reactor 10 and 34, recycle line 58 is passed through a suitable heat exchanger or cooler 64 which removes the heat of the oligomerization reaction from the recycling contents so as to maintain the temperature within loop recycle reactor 50 within the range of about 10° to about 50° C., preferably from about 20° to 30° C. With the use of ethanol as the preferred co-catalyst, optimum oligomerization is achieved by maintaining each of the loop recycle reactors at a temperature of about 25° C. Cooling water or brine can be effectively used in heat exchanger or cooler 64 to maintain the temperature within the above range.

As was the case with respect to the previously discussed loop recycle reactors, the recycle loop associated with loop recycle reactor 50 is such that the contents of loop recycle reactor 50 are turned over at least once every five minutes, preferably at least once every three minutes. Here again, there is no limit with respect to the speed at which the turnover can be achieved since a faster turnover effects a more efficient mixing of the boron trifluoride-promoter catalyst with the feedstock and partial oligomer product undergoing oligomerization. Again it is suggested that on a commercial scale, turnovers of the contents of each of the loop recycle reactors employed in the continuous oligomerization process can be achieved as quickly as 3–5 times each minute. This will provide very efficient mixing and efficient oligomerization.

As indicated in the figure, a portion of the contents of loop recycle reactor 50 recycling through line 58 is withdrawn from recycle line 58 through line 66, the flow being regulated by valve 68. In operation, the flow of oligomer product from recycle line 58 through line 66 will be essentially equivalent to the flow of alpha-olefin feed through line 12 into the first loop recycle reactor 10 so that there is a continuous flow of reactants and products through the loop recycle system. Generally, the total residence time of the materials within the loop recycle system of the present invention will be from about one to two hours; although somewhat shorter and longer residence times can be employed depending, of course, upon the conditions existing within the loop recycle reactor system and, in particular, the specific promoter of co-catalyst utilized in conjunction with the boron trifluoride. It has been found however, that with a residence time of from about one to two hours, an advantageous oligomerization product can be produced.

The crude oligomerization product withdrawn from recycle line 58 through line 66 will contain some unreacted alpha-olefin monomer, trimer, tetramer and some $C_{50}$ and higher oligomers. In addition, the crude oligomer product will contain the boron trifluoride-promoter complex. The removal of that complex from the oligomer product for reuse in the process of the present invention will be discussed hereinafter.

In order to obtain a synthetic lubricant of excellent properties from 1-decene, for example, it is desirable when carrying out alpha-olefin oligomerization to provide a product which has a high trimer content and a high ratio of trimer to tetramer. In the crude product resulting from the oligomerization it is desirable to obtain a ratio of trimer to tetramer of 2-½ to 1 or better, with optimum product properties being achieved with ratios of trimer to tetramer of 3:1 or better. Such ratios are achievable in accordance with the process of the present invention utilizing the loop recycle reactor system. For example, a typical crude oligomerization product obtained utilizing the conditions enumerated above can be represented as follows:

1-decane monomer: about 6 percent,
dimer: about 10 percent,
trimer: about 62 percent,
tetramer: about 20 percent,
$C_{50}+$: about 2 percent.

When such a product is further processed to remove essentially all but its trimer and tetramer components, a highly advantageous synthetic lubricant of approximately 85 percent trimer and 15 percent tetramer can be produced.

In typical alpha-olefin oligomerization processes, the crude oligomer product is subjected to one or more caustic washings and subsequent water washings to remove the boron trifluoride-promoter complex. Alternatively, a distillation procedure is utilized to remove this boron trifluoride-promoter complex from the crude oligomer product. Each of these procedures however, has inherent disadvantages of cost and catalyst loss. It is a unique characteristic of the process of the present invention that the more efficient mixing associated with the loop recycle reactor system allows the employment of complex catalyst systems which are less soluble in the alpha-olefin feed and oligomer product than typically used complex catalyst systems. One of these which has been found to be particularly effective in achieving an excellent product is the complex system formed by complexing boron trifluoride with ethanol as the promoter or co-catalyst. When ethanol is so employed in accordance with the preferred embodiment of the present invention, the boron trifluoride-ethanol complex can be removed from the crude oligomer product by physical means, such as by decantation. Preferably, however, in accordance with the invention developed by Fred S. Valentine and Gary W. Grams, the crude oligomer product in line 66 is passed into a suitable centrifuge 70 wherein physical separation of 90% or more of the boron trifluoride-ethanol complex from the crude oligomer product can be effectively achieved. To effect this separation, any conventional liquid-liquid centrifuge can be effectively employed. As illustrated in the figure, the boron trifluoride-ethanol complex which is removed from the crude oligomer product by means of centrifuge 70 is returned to recycle line 30 of loop reactor 10 through line 72 by means of pump 74 and valve 76.

The crude oligomer product exiting centrifuge 70 is forwarded for oligomer product finishing in the manner which is well known in the art and, consequently, not illustrated in the figure. This can include one or more caustic and/or water washings to remove any residual boron trifluoride-promoter complex which is not removed in centrifuge 70 and thereafter forwarded for further product finishing. In this respect, it is often desirable to substantially remove from the oligomer product the monomer and dimer content in order to avoid vaporization loss from a synthetic lubricant during its use. In some applications, however, it may be desirable to retain a substantial amount of dimer in the product, for uses involving low temperatures or a closed system, for example. In addition the dimer which is typically removed from the oligomer product can be oftentimes utilized as a separate product of commercial value. In order to produce a product of desirable viscosity and other properties as a synthetic lubricant, it is often desirable to remove the fraction of pentamer and higher oligomer; although here again, for particular purposes, it is often possible to retain these within the final oligomer product. All of these possibilities are conventional in the art, typically being carried out by suitable distillation.

In addition, the oligomer product is typically subjected to hydrogenation in order to stabilize the product and protect it from oxidative degradation. This hydrogenation is carried out either before or subsequent to dimer removal. Hydrogenation subsequent to dimer removal is often advantageous when the hydrogenated dimer is to be utilized as a useful product. Conventional hydrogenation catalysts such as palladium, platinum, nickel and the like at a suitable elevated temperature and pressure for hydrogenation, all conventional in the art can be typically employed. These procedures for finishing the oligomer product are described for example in U.S. Pat. No. 4,045,508 in the name of Barrett L. Cupples, et al, assigned to Gulf Research and Development Company.

Under the preferred conditions discussed above, the process of the present invention is typically carried out as follows. The decene is metered into the first reactor along with a co-catalyst or promoter and $BF_3$. The co-catalyst complexes with the $BF_3$ upon contact. The time for complexing is minimized due to the maximum liquid-gas surface area provided by the loop recycle reactor design. The decene and complex are mixed sufficiently to start the oligomerization reaction. The constant input of material into the first reactor causes the level to rise, activating a sensor, which opens a valve causing material to be forwarded from the recycle loop to the next reactor where the oligomerization continues. Heat exchangers on the recycle loops remove the heat caused by the reaction and the temperature is easily controlled due to the large surface area offered by the loop recycle reactor. As the liquid level in the second reactor rises, liquid is forwarded to the third reactor. Here the oligomerization is completed.

The amount of reaction taking place in each reactor is affected by several factors including residence time, catalyst concentration and mixing efficiency. Residence time is controlled by olefin feedrate into the first reactor and by the level in each reactor. Mixing efficiency can be improved by increasing recycle pump rate, using in-line static mixers on the recycle loop, and any other mechanical source.

The co-catalyst or promoter can be water, alcohol, or acid. A unique feature of this process is the use of an ethanol co-catalyst, which has poor solubility as a complex in the decene and therefore is easily separated from the crude oligomer. Following separation, the complex is then recycled to the first reactor, thereby greatly reducing the boron trifluoride consumption and resulting in significant reduction in catalyst expense. The crude oligomer is then forwarded for further finishing operation.

The present invention will now be described by reference to the following examples. In all cases, the examples were carried out on laboratory scale apparatus constructed to simulate the conditions which will exist in a commercial plant facility owned by Pearsall Chemical Company in LaPorte, Texas. The laboratory scale equipment was constructed to demonstrate the utilization of three loop recycle reactors in series for the oligomerization of alpha-olefins. Unless otherwise specified in the following examples, all percentages are by weight and all temperatures in °C.

EXAMPLES 1–4

Utilizing three loop recycle reactor laboratory scale equipment, the following experimental examples were carried out.

Example 1 was carried out to show how a commonly used promoter, like butanol, is soluble in decene and by premix the promoter can be introduced into the reaction at a constant concentration and maintain constant product quality.

Example 2 was carried out to illustrate that an attempt to premix ethanol in decene resulted in satisfactory product at the start of the reaction while the ethanol concentration was normal but a decreasing oligomer yield and increase in unreacted decene as the ethanol starts the fall out of the decene feed tank.

Example 3 illustrates improved oligomer yield by injecting ethanol directly into the first loop reactor.

Example 4 illustrates improved trimer/tetamer ratio by going to 25° C. reactor temperature instead of 20° C. The great effect of decreased mixing in the reactions as shown by the reduced oligomer yield was after reducing pumping rate.

The conditions and experimental results of Examples 1–4 are shown in the following Table 1.

TABLE 1

| Example No. | 1 | 2 | | 3 | 4 | |
|---|---|---|---|---|---|---|
| Promoter | Butanol | Ethanol | | Ethanol | Ethanol | |
| $BF_3$ Pressure | 10 psi | 10 psi | | 10 psi | 10 psi | |
| Reaction Temp. | 50° C. | 20° C. | | 20° C. | 25° C. | |
| Form of Promoter intro. | Premix in Decene | Premix in Decene | | Injected in R-1 cont. | Injected in R-1 cont. | |
| Promoter Conc. | 25cc/gal | 0.75% by wt. | | 0.75% by wt. | 0.75% by wt. | |
| Decene Forwarding Rate | 50cc/min | 50cc/min | | 50cc/min | 43cc/min | |
| Total Forwarding Time | 4 hr. | 4½ hr. | | 6 hr. | 12 hr. | |
| G.C. Analysis | | @1 hr. | @4 hr. | | @7 hr. | * |
| % Monomer | 4 | 7.8 | 12.9 | 5.4 | 7.2 | 20.8 |
| % Dimer | 15 | 8.1 | 8.3 | 5.1 | 9.8 | 12.0 |
| % Trimer | 58 | 59.0 | 54.8 | 61.6 | 61.0 | 52.5 |
| % Tetramer | 20 | 23 | 20.0 | 25.2 | 19.0 | 13.2 |
| % Pentamer | 3 | 3.1 | 4.0 | 2.7 | 3.0 | 1.3 |

*Final Product 2 hr. after reducing circulation rate in each reactor to ¼ of normal The foregoing examples illustrate the various advantages of the oligomerization process of the present invention utilizing a plurality of loop recycle reactors. In this regard, the excellent mixing which is achieved by the use of the loop recycle system allows for a more efficient oligomerization process and the production of an oligomer product having a desirable oligomer distribution. Moreover, the oligomerization reaction is simplified by eliminating, or substantially eliminating, such steps as caustic and water washing, by allowing the use of complex catalysts which are less soluble in the alpha-olefin feed and oligomer product. This produces higher levels of catalyst yield and higher efficiency in oligomerization. The absence of water in the system utilizing the preferred co-catalyst or promoter, is also advantageous.

Moreover, in accordance with the preferred embodiment of the present invention, better than 90% of the boron trifluoride-promoter complex can be separated and recycled by use of centrifugal separation. The process of the present invention is therefore economically attractive when compared with conventional oligomerization reactions.

While the present invention has been described primarily with respect to the description of preferred embodiments and specific examples above, it should be understood that the present invention cannot under any circumstances be deemed limited thereto but rather must be construed as broadly as any and all equivalents thereof.

What is claimed is:

1. In a process for the continuous production of an oligomer product having a desirable oligomer distribution, said process involving the oligomerization of a $C_8$-$C_{12}$ alpha-olefin monomer in the presence of a promoted boron trifluoride catalyst, the improvement wherein the oligomerization is carried out in a system comprising a plurality of loop recycle reactors in series, such that:
   (a) the total residence time of alpha-olefin monomer/oligomer product in said system is from about one to two hours; and
   (b) the flow rate through each of said plurality of loop recycle reactors affects a turnover of contents in each reactor at least once every five minutes.

2. The improved process of claim 1 wherein the flow rate through each of said plurality of loop recycle reactors affects a turnover of contents in each reactor at least once every three minutes.

3. The improved process of claim 1 wherein the height to diameter ratio of each of said loop recycle reactors is from 2:1 to about 12:1.

4. A process for the continuous production of an oligomer product having a desirable oligomer distribution which comprises:
   (a) continuously introducing into a first loop recycle reactor of a plurality of loop recycle reactors, in, series:
      (i) alpha-olefin feedstock;
      (ii) boron trifluoride; and
      (iii) a promoter for the boron trifluoride
   (b) establishing in said first loop recycle reactor a turnover of contents at least once every five minutes;
   (c) continuously withdrawing a portion of the contents of said first loop recycle reactor and forwarding said withdrawn portion to at least one additional loop recycle reactor;
   (d) continuously introducing into each of said additional loop recycle reactors further amounts of boron trifluoride;
   (e) establishing in each of said additional loop recycle reactors a turnover of contents at least once every five minutes; and
   (f) continuously withdrawing oligomer product from the last of said additional loop recycle reactors.

5. The process of claim 4 wherein the oligomerization is carried out in three loop recycle reactors in series.

6. The process of claim 4 wherein said alpha-olefin contains from 8 to 12 carbon atoms.

7. The process of claim 6 wherein said alpha-olefin is 1-decene.

8. The process of claim 4 wherein said promoter is selected from water, lower aliphatic alcohols, low molecular weight carboxylic acids, esters and ketones.

9. The process of claim 8 wherein said promoter is present in each of said plurality of loop recycle reactors in an amount of from about 0.01 weight % to about 3.0 weight % based on the weight of the alpha-olefin feedstock.

10. The process of claim 4 wherein boron trifluoride is present in each of said plurality of loop recycle reactors in an amount sufficient to saturate said alpha-olefin feedstock and promoter.

11. The process of claim 10 wherein each of said plurality of loop recycle reactors has a boron trifluoride pressure of from about 2 to about 100 psi.

12. The process of claim 4 wherein each of said plurality of loop recycle reactors is maintained at a temperature of from about 10° to about 50° C.

13. The process of claim 12 wherein the temperature of each of said plurality of loop recycle reactors is maintained within the range of 20°–30° C.

14. The process of claim 4 wherein the contents of each of said plurality of loop recycle reactors are turned over at least once every 3 minutes.

15. The process of claim 5 wherein the total residence time for said plurality of loop recycle reactors is from about 1 to 2 hours.

* * * * *